United States Patent

Cuckler et al.

[19]

[11] Patent Number: 5,931,870
[45] Date of Patent: Aug. 3, 1999

[54] ACETABULAR RING PROSTHESIS WITH REINFORCEMENT BUTTRESS

[75] Inventors: John M. Cuckler, Birmingham, Ala.; Joseph Schatzker; Allan E. Gross, both of Toronto, Canada; Constance E. Johnston, Eads; David C. Kelman, Collierville, both of Tenn.; Timothy McTighe, Chagrin Falls, Ohio

[73] Assignee: Smith & Nephew, Inc., Memphis, Tenn.

[21] Appl. No.: 08/727,948

[22] Filed: Oct. 9, 1996

[51] Int. Cl.[6] .................................. A61F 2/02; A61F 2/30; A61F 2/34; A61F 2/36
[52] U.S. Cl. .................................. 623/16; 623/18; 623/22; 623/23; 623/20; 623/19; 623/21
[58] Field of Search ........................... 623/16, 18, 19–23

[56] References Cited

U.S. PATENT DOCUMENTS

| 5,507,819 | 4/1996 | Wolf | 623/19 |
|---|---|---|---|
| 5,507,833 | 4/1996 | Bohn | 623/23 |
| 5,549,691 | 8/1996 | Harwin | 623/22 |
| 5,549,697 | 8/1996 | Caldarise | 623/22 |
| 5,584,880 | 12/1996 | Martinez | 623/4 |
| 5,609,646 | 3/1997 | Field et al. | 623/22 |
| 5,641,323 | 6/1997 | Caldarise | 623/22 |
| 5,658,338 | 8/1997 | Tullos et al. | 623/18 |
| 5,658,348 | 8/1997 | Rohr, Jr. | 623/22 |
| 5,676,704 | 10/1997 | Ries et al. | 623/18 |
| 5,702,475 | 12/1997 | Zahedi | 623/22 |
| 5,702,477 | 12/1997 | Capello et al. | 623/22 |
| 5,702,478 | 12/1997 | Tornier | 623/22 |
| 5,709,688 | 1/1998 | Salyer | 606/81 |

FOREIGN PATENT DOCUMENTS

| 0 563 503 | 3/1992 | European Pat. Off. | 623/22 |
|---|---|---|---|
| 88 07 947 | 9/1988 | Germany | 623/22 |
| WO 94/23670 | 10/1994 | WIPO | A61F 2/34 |
| WO 96/13231 | 5/1996 | WIPO | A61F 2/34 |

*Primary Examiner*—Mickey Yu
*Assistant Examiner*—Choon P. Koh
*Attorney, Agent, or Firm*—Garvey, Smith, Nehrbass, & Doody, L.L.C.

[57] ABSTRACT

A cemented acetabular prosthesis includes a cup body having a relative thin wall (for example, 2 mm). The body has a concave surface, a convex surface, and an annular rim. A plastic liner registers into a concavity of the cup body, the liner having a wall with a liner wall thickness much greater than the cup body wall thickness and a concave surface and a convex surface that registers and fits the concave surface of the cup body. The cup body wall provides a plurality of openings. Some of the openings are bone screw receptive openings that are reinforced with an annular reinforcement that extends away from the convex surface of the cup body. Other openings are unreinforced openings that allow cement to flow from the concave to the convex side of the cup body and into the patient's acetabulum during surgery. The cup body has a peripheral buttress portion for supporting a volume of cement of the cement mantle at a peripheral interface position between the liner and the body.

46 Claims, 7 Drawing Sheets

5,931,870

ACETABULAR RING PROSTHESIS WITH REINFORCEMENT BUTTRESS

BACKGROUND OF THE INVENTION

1. Field of the Invention

The present invention relates to medical orthopaedic surgical devices, and more particularly relates to an improved orthopaedic acetabular prosthesis with a reinforcement buttress to provide additional support for a cemented, all polyethylene cup prosthesis.

2. General Background

Acetabular defects have thus been treated by many different methods. Some of these methods include filling the void with bone cement; bone grafting; and implanting bipolar prostheses, custom designed implants, and cementless acetabular components. However, each of these methods has had problems treating massive bone deficiencies. Reinforcement rings are designed to address the failure modes seen in the previously mentioned methods. Reinforcement rings have been used clinically for many years to treat massive bone deficiencies. They can be used with or without bone grafts depending on the degree and position of the defect. Anti-protrusio cages are discussed in an article authored by Berry and Müller, entitled "Revision Arthroplasty Using An Anti-Protrusio Cage for Massive Acetabular Bone Deficiency," Journal of Bone and Joint Surgery, Vol. 74-B, No. 5, September 1992, pp. 711–715.

Some acetabular defects create problems for a surgeon when implanting an acetabular prosthesis. These defects often dictate that a artificial acetabular cavity be created to receive an artificial acetabular socket utilizing a grouting agent to secure the socket in place.

One of the problems with certain patients having pelvic defects is that of a lack of available host bone tissue for receiving and connecting to the prosthesis. Rings are used with screws fixated to either bone graft or host bone. Cement is then used with the "all poly" component.

In bone defect cases, cement does not always have proper support to hold the polyethylene or "poly" liner. Such bone defects can be in the form of gaps in the bone, or columnar defects such as a posterior column defect.

There are a number of commercially available acetabular prosthetic devices that include a cup shaped body. Reinforcement shells include Protek's Müller acetabular roof reinforcement ring and the Howmedica Oh-Harris Protrusio Shell. Reconstruction shells include Protek's H. B. Burch—R. Schneider Reinforcement Cage (C. P. Titanium), Protek's R. Ganz Acetabular Roof Reinforcement Ring with Hook (C. P. Titanium), and Osteonics' Gap Acetabular Cup (C. P. Titanium). Some of these acetabular cups have correspondingly shaped inner and outer concave and convex surfaces. Some devices have projections extending from the outer surface of the cup-shaped body. For example, U.S. Pat. No. 3,939,497 describes a socket for a hip joint prosthesis which is secured to a cavity in the bone tissue by a series of radially arranged pegs which can be projected outwardly from the wall of the socket into the surrounding tissue by a central screw which also has a self-tapping thread that enters the tissue.

European Patent Application No. 169,978 published May 2, 1986, describes an acetabular cup which has an outer shell embedded into the patient's pelvis. The outer shell has a frustro-conical skirt and a spherical central cap.

In European Patent Application No. 211,169 published Feb. 25, 1987, an acetabular cup is described in which an external boss protrudes from the outer surface of the acetabulum body to fit into a pre-drilled hole in the acetabulum.

Other foreign patents and patent applications which describe acetabular cups include European Patent Application No. 212,087 published Apr. 3, 1987, wherein metallic pins project from the surface of the cup and contain holes in which tissue may grow. In European Patent No. 341,198 published Nov. 8, 1989, an acetabular cup has a metal outer shell and a plastic body for retaining the hip joint head.

Some acetabular cup devices have outer surfaces with two differently shaped regions thereon including an annular rim or skirt that is thickened for forming an interference fit with the pelvis. Another acetabular cup (Patent DE 3341723C1) is in the form of a hemispherical socket body that is flattened at the crown region, to ensure lateral wedging of the socket in the pelvic bone.

SUMMARY OF THE INVENTION

The Acetabular Reinforcement/Reconstruction Shell System consists of a "Roof Reinforcement" shell and a "Reconstruction" shell. Both types have multiple screw holes for fixation. Acetabular Reinforcement/Reconstruction Shells are manufactured from commercially pure titanium in a variety of sizes to accommodate the needs of all patients. The metal shell is positioned with screws and then an all polyethylene component is cemented into place. By incorporating a construct that includes a metal shell, screws, cement and an all poly component, the system provides more strength than only cement or bone grafting.

The Reconstruction Shell consist of a full or partial cup shaped device with multiple angled and/or twisted flanges for fixation in the ilium or ischium. This device has a reinforcement cement buttress which acts as a form of support for the cemented all polyethylene cup which is typically left unsupported in this area. A third flange can be fixated to the posterior column.

The present invention thus provides an improved (cemented) acetabular prosthesis that includes a cup body having a thin wall with a cup body wall thickness of about 2 mm. The body has a concave surface, a convex surface, and an annular rim.

The concave surface of the ring allows for the use of a cemented "all poly" component. The polyethylene or "all poly" then accepts the femoral head of a hip stem.

The cup body wall provides a plurality of openings therethrough. Some of these openings are bone screw receptive openings that are reinforced with an annular reinforcement that extends away from the convex surface of the cup body. Others of the openings are openings that allow cement to flow through the concave and convex layers of the cup body. A threaded hole accepts a correspondingly threaded instrument that allows for ring insertion.

A cement mantle is used to affix the plastic liner within the cup body. The cement mantle flows through at least some of the openings upon use of the cup liner. Others of the openings that are reinforced are used for receiving bone screws that attach the cup body to the patient's pelvis.

In a first embodiment (acetabular roof reinforcement shell), at least one curved annularly extending flange extends away from the rim of the cup and helps attach the cup body to the patient's pelvis. The reinforcement buttress helps secure a mass of cement in between the cup body and the polymeric liner.

In a second embodiment (acetabular reconstruction shell), a plurality of radially and circumferentially spaced flanges (preferably three) extend away from the cup body. One of the flanges is an inferior flange. Opposite the inferior flange are two additional flanges, a superior flange and a posterior flange. In the second embodiment, a buttress extends a partial distance around the rim of the cup and is preferably positioned adjacent to the superior and posterior flanges.

BRIEF DESCRIPTION OF THE DRAWINGS

For a further understanding of the nature and objects of the present invention, reference should be had to the following detailed description, taken in conjunction with the accompanying drawings, in which like parts are given like reference numerals, and wherein.

DETAILED DESCRIPTION OF THE PREFERRED EMBODIMENT

Figure 1:
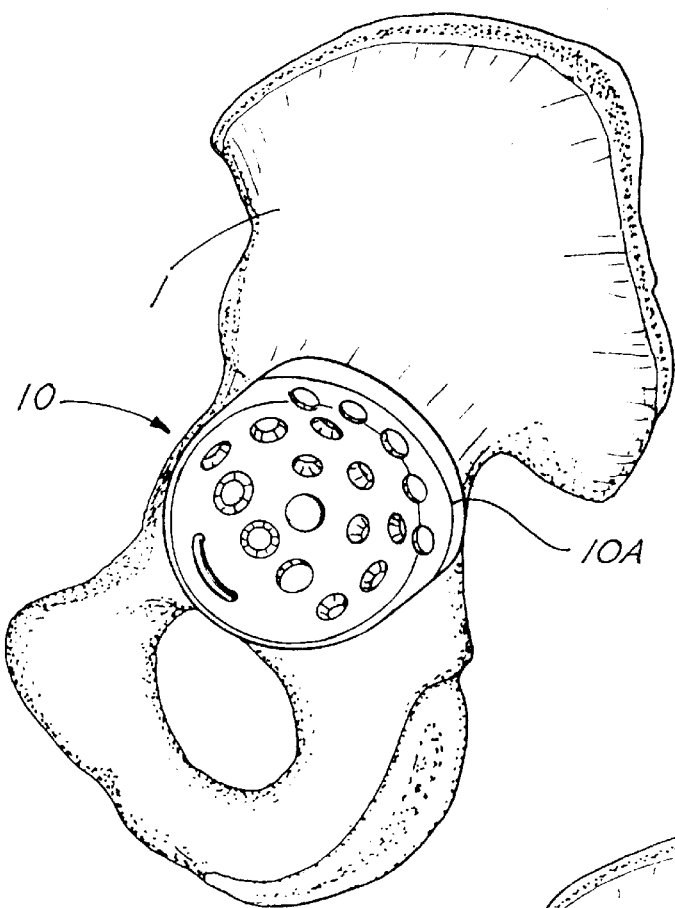
FIG. 1 is a top schematic view of the first embodiment of the apparatus of the present invention.
Figure 2:
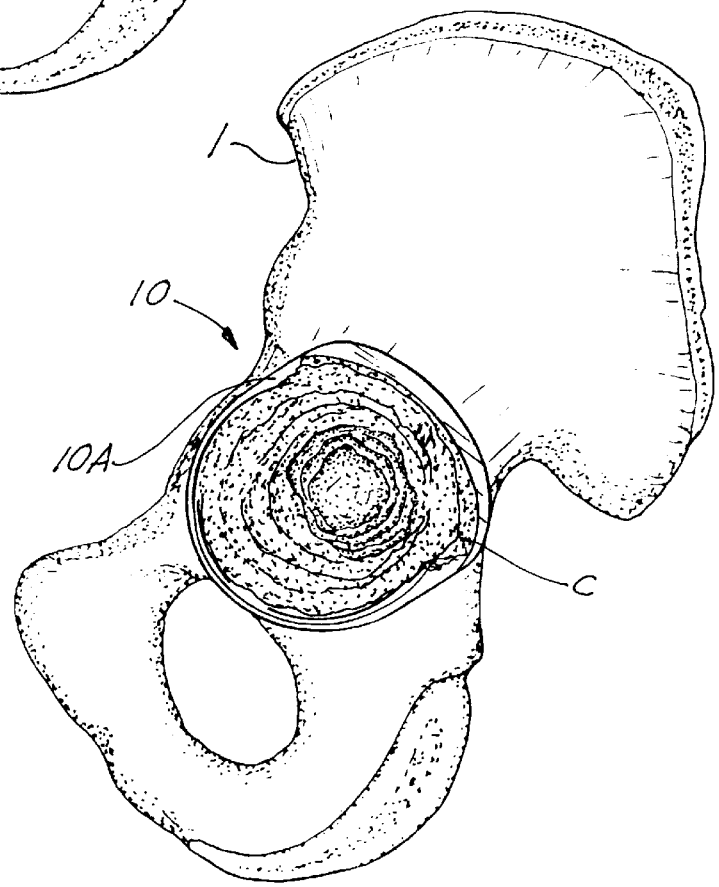
FIG. 2 is another top view of the first embodiment of the apparatus of the present invention after the application of bone cement and prior to receiving the plastic liner.
Figure 3:
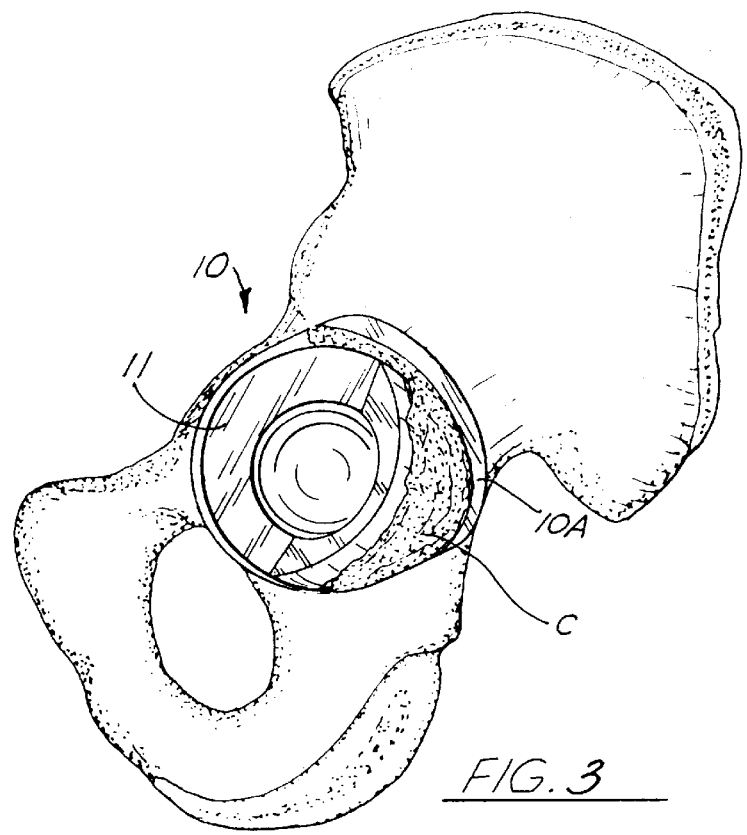
FIG. 3 is schematic perspective view of the first embodiment of the apparatus of the present invention showing the plastic polymeric liner in its cemented position.
Figure 4:
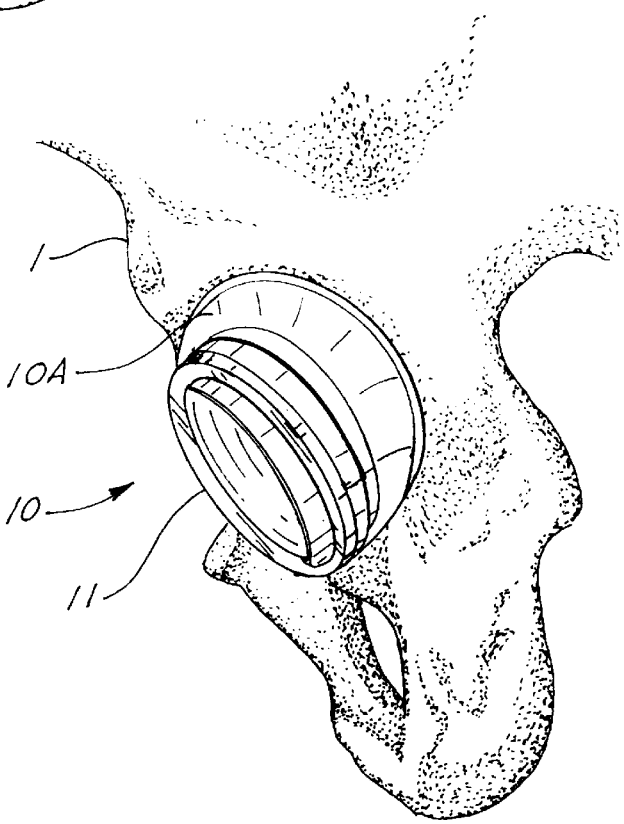
FIG. 4 is another perspective view of the first embodiment of the apparatus of the present invention showing the liner in cemented position.

FIGS. 1 and 2 show the first embodiment of the apparatus of the present invention designated generally by the numeral 10. Acetabular prosthesis 10 includes a cup body 10A that can be placed in the acetabulum of a patient's pelvis 1 as shown in FIGS. 1 and 2. In FIGS. 3 and 4, a plastic liner 11 has been placed into concave surface portion 12B of the cup body 10A. A mass of cement C is then used to hold the polyethylene "all poly" plastic component 11 to the cup body 10A after the cup body 10A has been secured to the patient's pelvis 1 as will be described more fully hereinafter.

In FIGS. 5–11, the first embodiment of the apparatus of the present invention is shown, designated generally by the numeral 10A. The cup body 10A has a pair of opposed surfaces 12A, 12B. The surface 12A is an outer surface that will abut the patient's acetabulum. The surface 12B is an inner surface that will abut and receive the plastic liner 11. A rim surface 13 extends a partial distance around the cup body 10A. Rim surface 13 defines a flat plane 13A.

Figure 5:
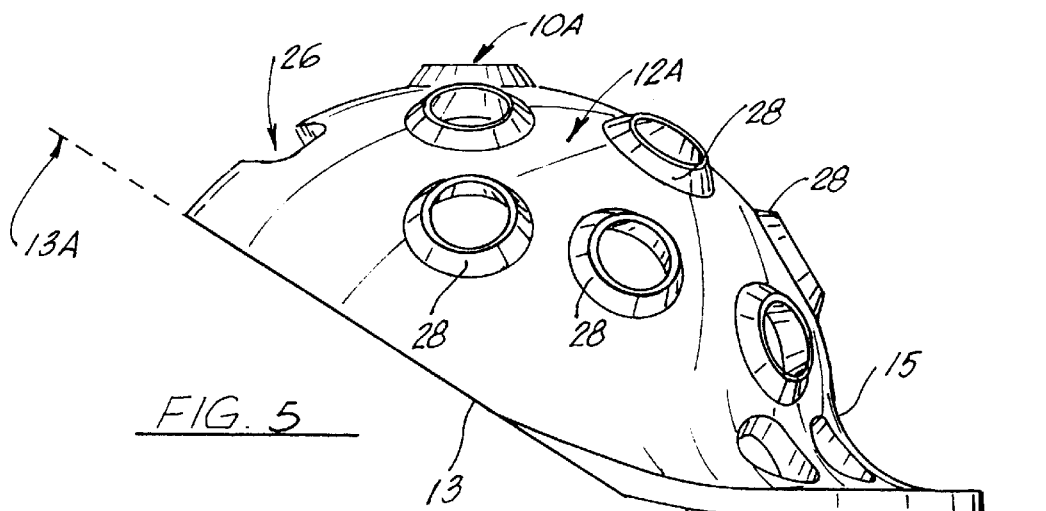
FIG. 5 is a side view of the first embodiment of the apparatus of the present invention showing the cup body.
Figure 6:
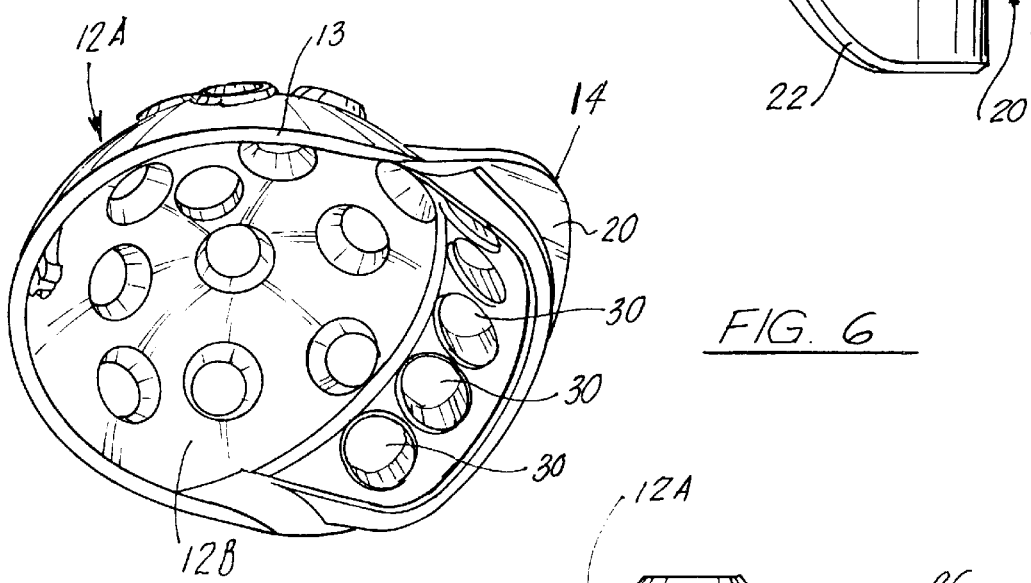
FIG. 6 is a bottom perspective view of the first embodiment of the apparatus of the present invention showing the cup body.
Figure 7:
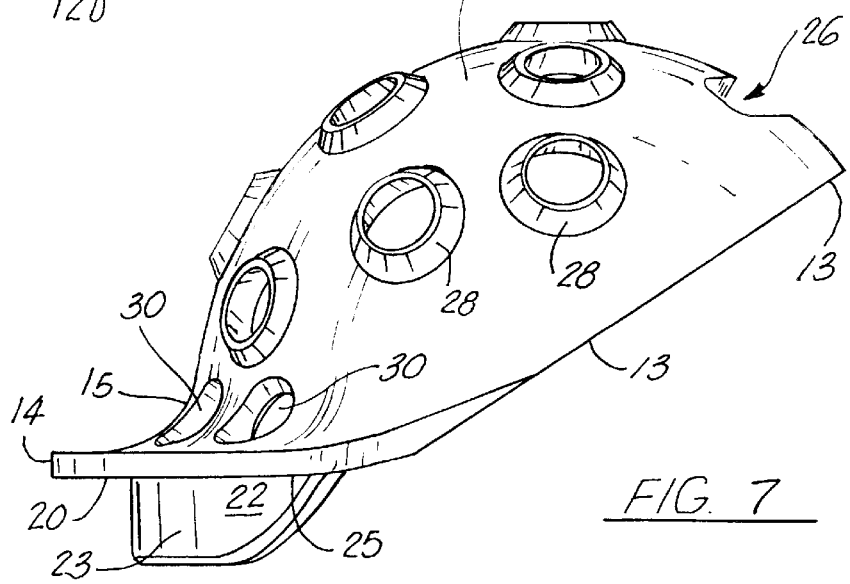
FIG. 7 is another side view of the first embodiment of the apparatus of the present invention showing the cup body.
Figure 8:
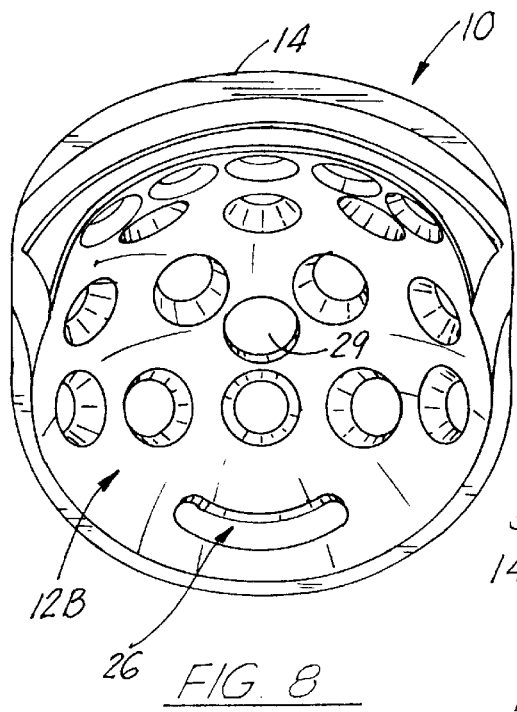
FIG. 8 is a bottom view of the first embodiment of the apparatus of the present invention.
Figure 9:
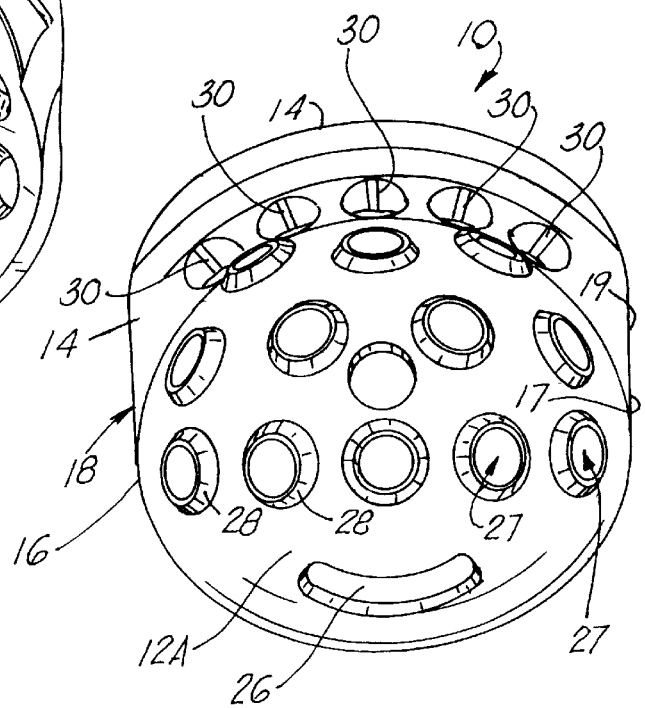
FIG. 9 is a top view of the first embodiment of the apparatus of the present invention.
Figure 10:
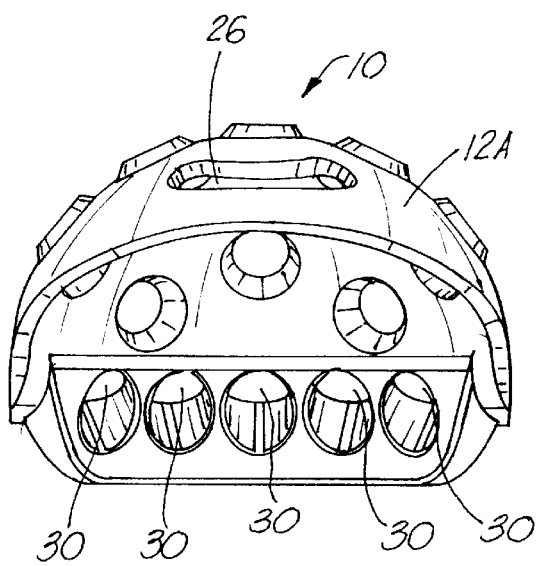
FIG. 10 is a front view of the first embodiment of the apparatus of the present invention.
Figure 11:
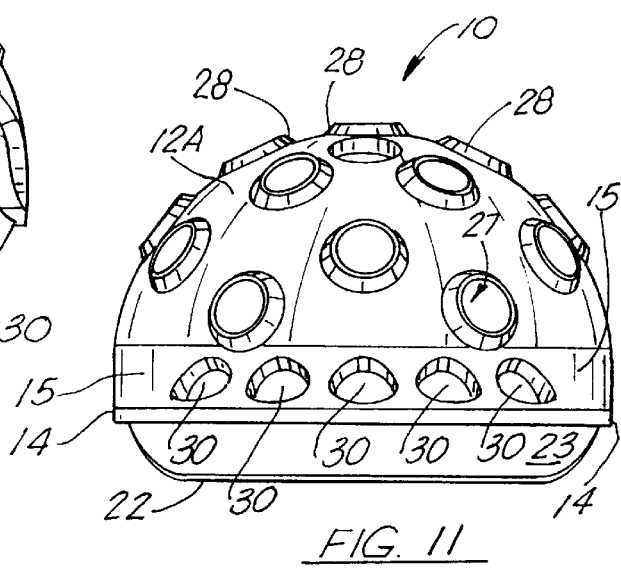
FIG. 11 is a rear view of the first embodiment of the apparatus of the present invention.

Flange 14 has a reverse curve portion 15 that joins with cup convex surface 12A, as shown in FIGS. 5 and 7. Flange 14 has end portions 16, 17 that define the transition connection to annular rim 13 of cup body 10A. Flange 14 has a pair of opposed outer edges 18, 19. The outer edges 18, 19 can be parallel.

Flange 14 has a lower surface 20 and a periphery 21. A curved buttress 22 is attached to flange 14 at its lower surface 20. This can be a one piece integral construction. Wall 22 has a curved outer surface 23 and a curved inner surface 24.

A flat plane 25 is defined by surface 20 of flange 14. In FIG. 5, the plane 25 of flange 14 and the plane 13A of rim 13 form an obtuse angle of about 147 degrees.

A number of openings are formed through cup body 10A. These openings include reinforced openings as well as unreinforced openings. One of the openings is in the form of an arcuate slot 26. Openings 27 are reinforced openings, being surrounded by a thickened portion of the cup body 10A at opening 27 in the form of an annular boss 28. Opening 29 is a threaded hole opening, having no reinforcement or annular boss 28 that surrounds it. Opening 29 is threaded to accept a positioning instrument for properly locating and impacting the cup body 10A.

Openings 30 are a plurality of openings, as shown in FIGS. 6 and 9, 10 and 11, that are formed through the reverse curved portion of the cup body 10A that forms a transition between flange 14 and the remainder of the cup body 10A, as shown in FIGS. 5 and 7.

Figure 12:
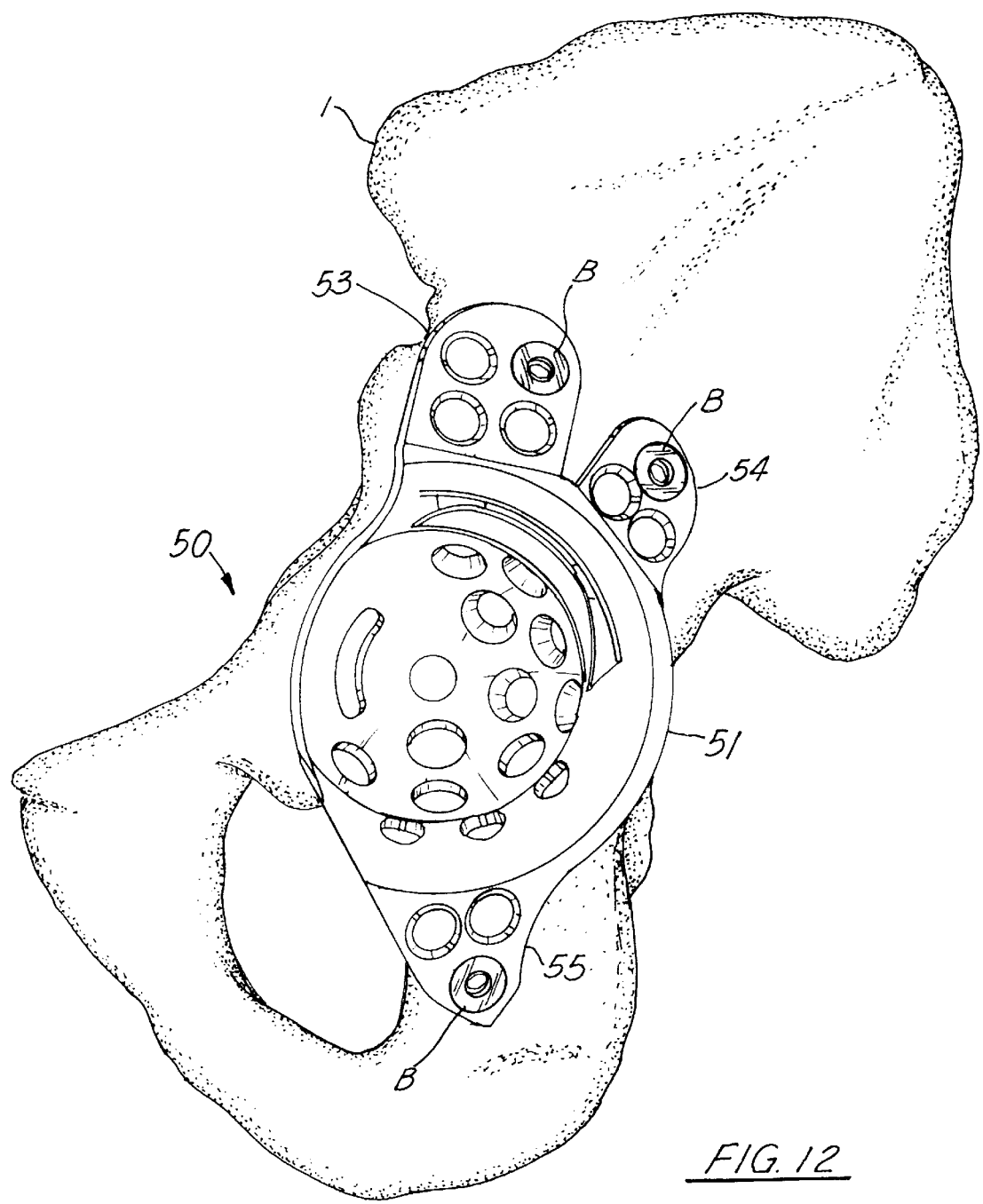
FIG. 12 is a top perspective view of the second embodiment of the apparatus of the present invention.

FIGS. 12–19 show a second embodiment of the apparatus of the present invention designated generally by the numeral 50. In FIG. 12, the cup prosthesis 50 is shown mounted in a patient's pelvis 1 at the acetabulum. The prosthesis 50 includes a cup body 51 that attaches to the pelvis 1 using a plurality of radially extending and circumferentially-spaced flanges 53, 54, 55.

In FIGS. 13–19, the three flanges 53, 54, and 55 are shown extending from the rim 52 of cup body 51. The flange 53 is the superior flange. The flange 54 is the posterior flange. The flange 55 is the inferior flange.

Figure 13:
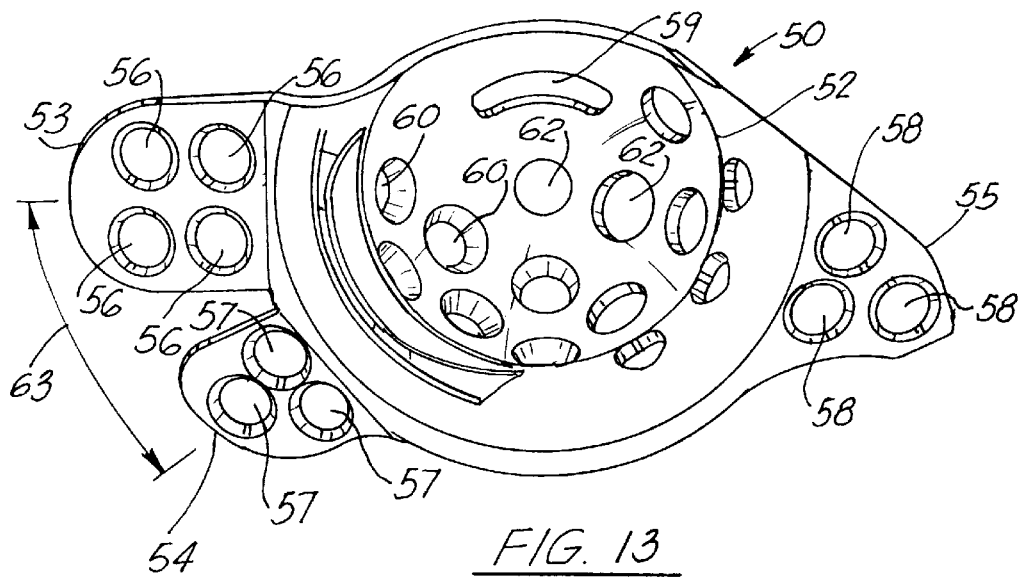
FIG. 13 is a top view of the second embodiment of the apparatus of the present invention.

The cup body 51 has an inner concave surface 51A that receives bone cement which receives an acetabular socket 11 as with the first embodiment 10. The cup body 51 also provides a convex surface 51B that fits the patient's acetabulum. Annular rim 52 extends around the periphery of cup body 51. Flanges 53, 54, 55 extend from annular rim 52 and are radially extending and circumferentially spaced about the rim 52 as shown in FIG. 13. Each of the flanges 53–55 provides one or more bone screw openings. The flange 53 has a plurality of openings 56. The flange 54 has a plurality of openings 57. The flange 55 has a plurality of openings 58. The openings 56–58 can be used to fasten the cup body 51 to the patient's pelvis 1 using fasteners such as the bone screws B shown in FIG. 12.

A buttress 65 extends a partial distance around the rim 52 of cup body 51 as shown in FIGS. 13 and 15–19. The buttress 65 can be used to contain bone cement in a mass to aid in holding the polyethylene {"all poly") liner 11 in position. An arcuate slot 59 extends through the cup body 51. Further, a plurality of openings 60, 62 extend through the cup 51 wall at spaced apart locations.

Figure 14:
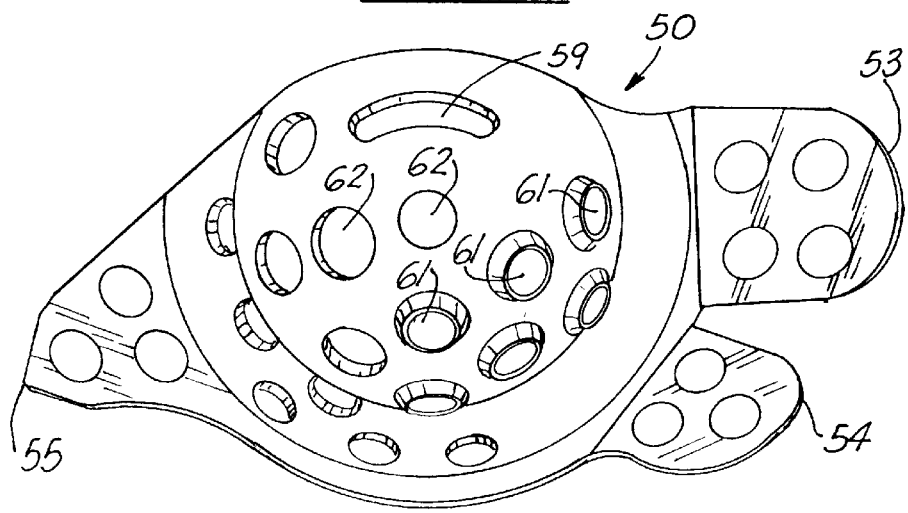
FIG. 14 is a bottom view of the second embodiment of the apparatus of the present invention.
Figure 15:
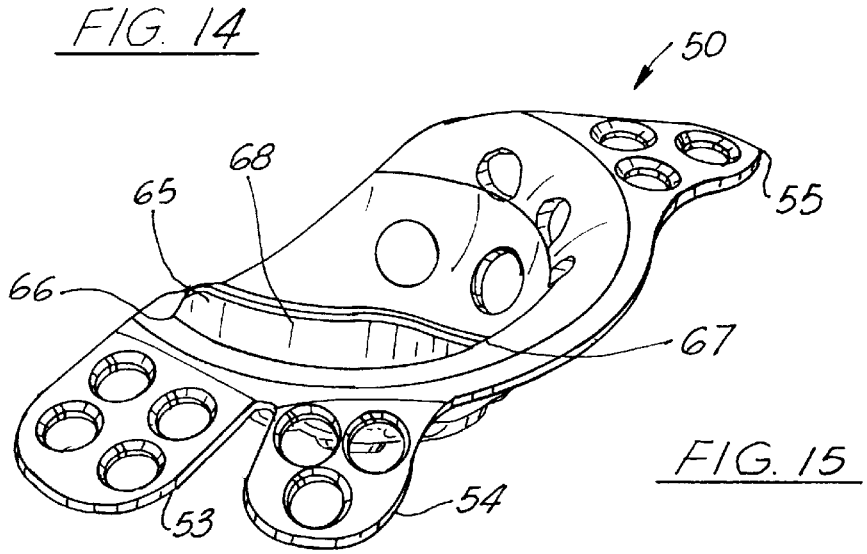
FIG. 15 is a top perspective view of the second embodiment of the apparatus of the present invention.
Figure 16:
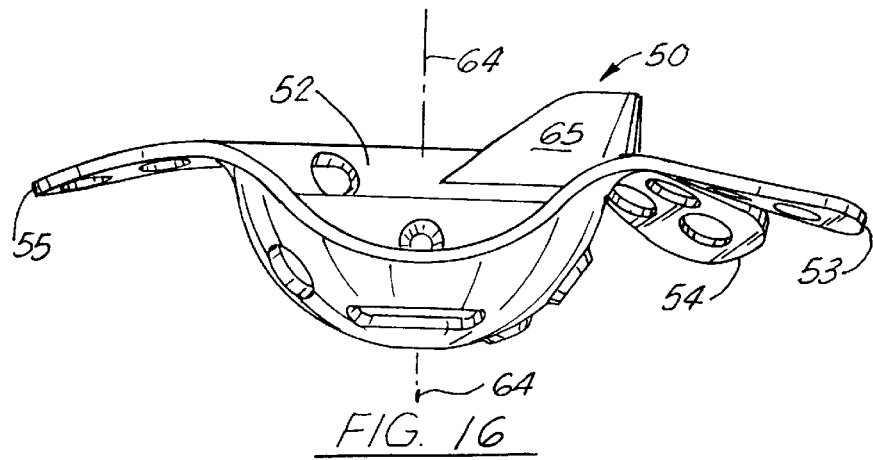
FIG. 16 is a side view of the second embodiment of the apparatus of the present invention.
Figure 17:
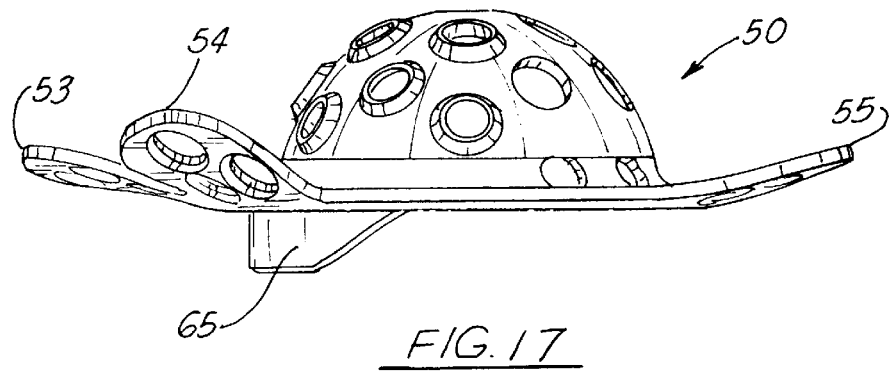
FIG. 17 is another side view of the second embodiment of the apparatus of the present invention.
Figure 18:
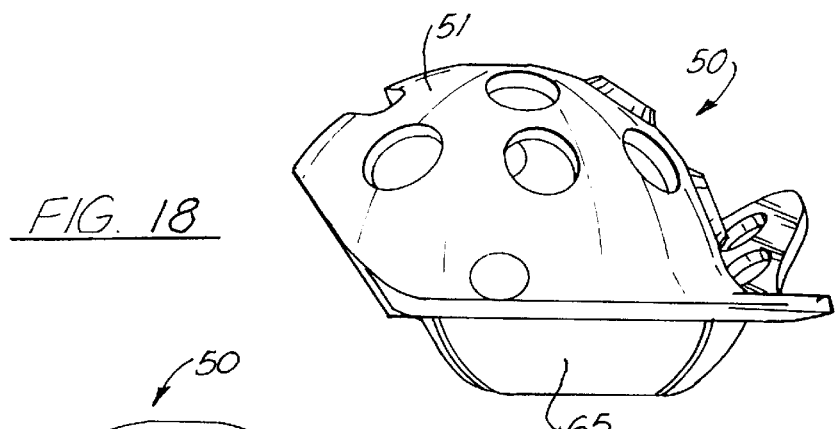
FIG. 18 is an end view of the second embodiment of the apparatus of the present invention.
Figure 19:
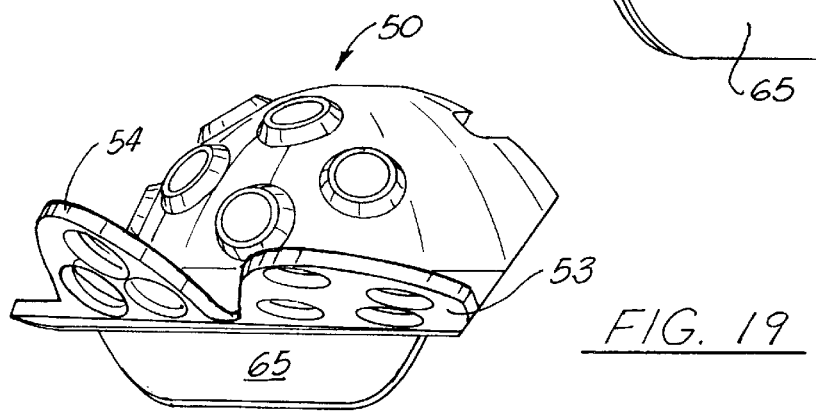
FIG. 19 is another end view of the second embodiment of the apparatus of the present invention.

Openings 60 are reinforced openings, being surrounded by a thickened portion of the cup body wall in the form of an annular boss 61. The annular boss 61 preferably extends from the convex or outer surface of cup body 51 as shown in FIG. 14. The screw holes 62 and the arcuate slot 59 are unreinforced openings that are designed to allow cement to flow freely from one side of the cup body to the other during the surgical procedure.

The following table lists the parts numbers and parts descriptions as used herein and in the drawings attached hereto.

PARTS LIST

| Part Number | Description |
|---|---|
| 10 | pelvic girdle |
| 10 | acetabular prosthesis |
| 10A | cup body |
| 11 | plastic liner |
| 12A | convex surface |
| 12B | concave surface |
| 13 | annular rim |
| 13A | rim plane |
| 14 | flange |
| 15 | reverse curve surface |
| 16 | end portion of flange |
| 17 | end portion of flange |
| 18 | outer edge |
| 19 | outer edge |
| 20 | lower surface of flange |
| 21 | periphery of flange |
| 22 | buttress |
| 23 | curved outer surface |
| 24 | curved inside surface |
| 25 | flat plane |
| 26 | arcuate slot |
| 27 | opening |
| 28 | annular boss |
| 29 | opening |
| 30 | opening |
| 50 | acetabular prosthesis |
| 51 | cup body |
| 51A | concave surface |
| 51B | convex surface |
| 52 | annular rim |
| 53 | superior flange |
| 54 | posterior flange |
| 55 | inferior flange |
| 56 | openings |
| 57 | openings |
| 58 | openings |
| 59 | arcuate slot |
| 60 | opening |
| 61 | annular boss |
| 62 | opening |
| 63 | angle |
| 64 | axis |
| 65 | wall |
| 66 | end of wall |
| 67 | end of wall |
| 68 | top of wall |

Because many varying and different embodiments may be made within the scope of the inventive concept herein taught, and because many modifications may be made in the embodiments herein detailed in accordance with the descriptive requirement of the law, it is to be understood that the details herein are to be interpreted as illustrative and not in a limiting sense.

What is claimed as invention is:

1. An acetabular prosthesis for cement implantation comprising;
    a) prosthesis full or partial cup body having a cup body wall with a cup body wall thickness, the body having a concave surface on a distal side of the cup body, a convex surface on a promimal side of the cup body and an annular rim;
    b) a liner that registers with the cup body, the liner having a liner wall with a liner wall thickness much greater than the cup body wall thickness and a concave surface and a convex surface that registers within the concave surface of the cup body;
    c) the cup body wall having a plurality of openings therethrough;
    d) some of the openings being bone screw receptive openings that are reinforced with an annular reinforcement positioned on the distal side of the cup body;
    e) a cement mantle for affixing the plastic liner to the cup body;
    f) the cup body having a peripheral buttress portion for supporting a portion next to the annular rim and extending distally downwardly from the concave surface, of cement of the cement mantle at a peripheral interface position in between the liner and body;
    g) wherein the cement mantle flows through at least some of the openings upon assembly of the cup liner to the cup body.

2. The prosthesis of claim 1 further comprising at least one flange that extends away from the rim of the cup body, for attaching the cup body to the patient's pelvis.

3. The prosthesis of claim 1 wherein the cup body is about 2 mm in thickness.

4. The cemented acetabular prosthesis of claim 1 wherein the cup body is hemispherically shaped.

5. The cemented acetabular prosthesis of claim 1 wherein the cup body is a partial hemispherical shape.

6. The cemented acetabular prosthesis of claim 1 wherein the liner has a plastic surface.

7. The cemented acetabular prosthesis of claim 1 wherein the liner is plastic.

8. The prosthesis of claim 1 further comprising an arcuate slot that extends through the cup body wall along and near the periphery of the cup body.

9. The prosthesis of claim 1 wherein the buttress extends a partial distance about the periphery of the cup body for supporting cement at the interface of the cup body and the liner.

10. The prosthesis of claim 1 wherein the buttress extends at least 45 degrees about the periphery of the rim of the cup body.

11. The prosthesis of claim 1 wherein the buttress at least 90 degrees about the periphery of the rim of the cup body.

12. The prosthesis of claim 1 further comprising an annular reinforcement that surrounds each opening.

13. An acetabular prosthesis for cement implantation comprising;
    a) a thin prosthesis cup body having a wall with a thickness of between 1 and 3 mm, the body having a distal concave surface area, a central portion, a proximal convex surface, and an annular rim defining a cup periphery;

b) the cup body having at least a pair of flanges that extend away from the cup central portion;

c) a plastic liner that can be cemented to the concave surface area of the cup body, the liner having a wall with a thickness much greater than the thickness of the cup body and a concave surface and a convex surface that registers with the concave surface area of the cup body;

d) the cup body wall having a plurality of openings therethrough;

e) some of the openings being bone screw receptive openings that are reinforced with an annular reinforcement that extends away from the convex surface of the cup body;

f) a cement mantle for affixing the plastic liner to the cup body;

g) the cup body having a peripheral buttress extending downwardly from the distal side of the cup body for supporting a portion of cement of the cement mantle at a peripheral interface position in between the liner and body; and h) wherein the cement mantle flows through at least some of the openings upon assembly of the cup liner to the cup body.

14. A acetabular cup prosthesis comprising:

a) a cup member having an inner, distal concave surface and an outer, proximal convex surface;

b) the cup member having an apex and a rim that extends about the periphery of the cup member, the rim having a portion that defines a rim plane;

c) a curved flange portion that extends a partial distance around the cup member and away from the convex surface of the cup member, the flange portion having lower surface and an edge that falls in a flange plane that forms an angle with the rim plane; and d) a buttress mounted on the distal concave surface of the cup body and at the lower surface of the flange portion and that extends distally downwardly from the flange portion, the buttress being curved to generally follow the curved flange member.

15. The acetabular cup prosthesis of claim 14 wherein the flange member and buttress each extend around the cup member a measure of between about 45 and 135 degrees.

16. The acetabular cup prosthesis of claim 14 wherein the flange member and buttress each extend around the cup member a measure of at least ninety degrees.

17. The acetabular cup prosthesis of claim 14 wherein the flange member forms a reverse curved portion with the convex outer surface of the cup member.

18. The acetabular cup prosthesis of claim 14 wherein the flange plane and the rim plane form an angle of between about 90 and 180 degrees.

19. The acetabular cup prosthesis of claim 14 further comprising at least one opening through the cup member.

20. The acetabular cup prosthesis of claim 14 further comprising a plurality of openings extending through the cup member.

21. The acetabular cup prosthesis of claim 14 further comprising at least one opening through the cup member and a bone screw for fastening the cup member to a patient's bone tissue at the opening.

22. The acetabular cup prosthesis of claim 14 further comprising a plurality of openings extending through the cup member, a bone screw for fastening the cup member to a patient's bone tissue at one of openings, and some of the openings being receptive of bone cement and for conveying bone cement between the inner concave and outer convex surfaces of the cup member.

23. A acetabular cup prosthesis comprising:

a) a thin cup member having a distal side with an inner concave surface, a proximal side with an outer convex surface, and a cup wall;

b) the cup member having an apex and a rim that extends about the periphery of the cup member, the rim having a portion that defines a rim plane;

c) a curved flange portion that extends a partial distance around the cup member and away from the convex surface of the cup member, the flange portion having lower surface and an edge that falls in a flange plane that forms an obtuse angle with the rim plane; and d) a buttress mounted on the distal side at the lower surface of the flange portion and that extends distally downwardly from the flange portion, the buttress being curved.

24. The acetabular cup prosthesis of claim 23 wherein the cup wall has a thickness of about 2 mm.

25. The acetabular cup prosthesis of claim 23 further comprising a bone screw and wherein the cup wall has an opening that receives the bone screw.

26. The acetabular cup prosthesis of claim 25 further comprising an annular boss that surrounds the bone screw opening.

27. The acetabular cup prosthesis of claim 23 further comprising an annular boss that surrounds the bone screw opening on the convex surface of the cup member.

28. The acetabular cup prosthesis of claim 24 further comprising a plurality of openings including at least some openings that are reinforced with thickened annular portions of the wall next to the openings, a bone screw, and wherein the bone screw fits the opening.

29. The acetabular cup prosthesis of claim 24 further comprising a plurality of openings extending through the cup member, at least some of the openings being surrounded by thickened portions of the cup member.

30. The acetabular cup prosthesis of claim 29 wherein the thickened portions are on the convex surface of the cup member.

31. The acetabular cup prosthesis of claim 24 further comprising a slot that extends through the cup member and about the cup member a distance.

32. The acetabular cup prosthesis of claim 24 wherein the flange member extends around the cup member a measure of between about 45 and 135 degrees.

33. The acetabular cup prosthesis of claim 24 wherein the flange member forms a reverse curved portion with the convex outer surface of the cup member.

34. The acetabular cup prosthesis of claim 24 further comprising a plurality of openings extending through the cup member at the flange portion.

35. A acetabular cup prosthesis comprising:

a) a cup member having a distal side with an inner concave surface and a proximal side with an outer convex surface;

b) the cup member having an apex and a rim that extends about the periphery of the cup member, the rim having a portion that defines a rim plane;

c) a plurality of circumferentially spaced, radially extending flange portions that each extend a partial distance around the cup member and away from the cup rim; and d) a buttress mounted on the distal surface of the cup member, and that extends distally downwardly from the rim plane.

36. The acetabular cup prosthesis of claim 35 wherein the buttress is curved to follow the rim.

37. The acetabular cup prosthesis of claim 35 wherein the buttress extends about 105–115 degrees about the cup member along a curved path.

38. The acetabular cup prosthesis of claim 35 wherein each flange extends around the cup member a measure of between about 20 and 45 degrees.

39. The acetabular cup prosthesis of claim 35 wherein each flange has at least one opening therethrough.

40. The acetabular cup prosthesis of claim 35 wherein there are between one and three flanges.

41. The acetabular cup prosthesis of claim 36 wherein at least some of the flanges form an acute angle with the rim plane.

42. The acetabular cup prosthesis of claim 36 wherein at least some of the flanges form an angle with the rim plane of between about 15 and 45 degrees.

43. The acetabular cup prosthesis of claim 40 wherein two of the flanges are on opposite sides of the cup member.

44. The acetabular cup prosthesis of claim 40 wherein the flanges include at least an inferior flange and another flange generally opposite the inferior flange.

45. The acetabular cup prosthesis of claim 40 wherein the flanges include inferior, posterior, and superior flanges.

46. The acetabular cup prosthesis of claim 45 wherein the inferior flange is opposite the posterior and superior flanges.

\* \* \* \* \*